United States Patent [19]

Bower et al.

[11] 3,962,278

[45] June 8, 1976

[54] N,N'BIS(PHTHALIC ANHYDRIDE) DIIMIDES

[75] Inventors: George M. Bower, Pittsburgh; Richard M. Skena, Murrysville, both of Pa.

[73] Assignee: Westinghouse Electric Corporation, Pittsburgh, Pa.

[22] Filed: Nov. 5, 1973

[21] Appl. No.: 413,073

Related U.S. Application Data

[62] Division of Ser. No. 97,334, Dec. 11, 1970, abandoned.

[52] U.S. Cl. .................... 260/326 C; 260/32.6 NA; 260/281 D; 260/281 F; 260/250 BC; 260/326 N; 260/326 S; 260/326.26; 428/435

[51] Int. Cl.$^2$............... C07D 405/14; C07D 471/06; C07D 487/04; C07D 487/14

[58] Field of Search........ 260/326 N, 326 C, 281 D, 260/281 F, 326.26, 250 BC, 326 S

[56] References Cited
FOREIGN PATENTS OR APPLICATIONS

| | | |
|---|---|---|
| 1,511,446 | 2/1966 | France |
| 1,192,001 | 5/1970 | United Kingdom |
| 1,317,952 | 5/1973 | United Kingdom |
| 1,283,077 | 7/1972 | United Kingdom |
| 1,162,203 | 8/1969 | United Kingdom |
| 973,377 | 10/1964 | United Kingdom |
| 1,169,569 | 11/1969 | United Kingdom |
| 189,830 | 12/1966 | U.S.S.R............................ 260/326 C |

OTHER PUBLICATIONS

Mifune et al. CA 68, 105,686k (1968).

*Primary Examiner*—Alton D. Rollins
*Assistant Examiner*—Mark L. Berch
*Attorney, Agent, or Firm*—A. Mich, Jr.

[57] ABSTRACT

Thermoplastic imide polymers prepared from a dianhydride monomer containing imide linkages and at least two cyclic anhydride groups and an aromatic diamine such as 4,4'-diaminodiphenyl ether. Comonomers such as 3,4:3',4'-benzophenonecarboxylic dianhydride may be added. Preferably said dianhydride monomer containing imide linkages is made by reacting 4-aminophthalic acid with a dianhydride containing at least two cyclic anhydride groups, preferably in the ratio of about 2:1. Preferably said imide polymer is made by first forming a solution containing the diamine and adding the dianhydride monomer containing imide linkages while the temperature of the solution is maintained between 50° and 120°C. and most preferably at 110°C.

5 Claims, No Drawings

N,N'BIS(PHTHALIC ANHYDRIDE) DIIMIDES

This is a division, of application Ser. No. 97,334 filed Dec. 11, 1970, now abandoned.

The invention relates to imide polymers prepared from dianhydride having imide linkages and, in particular, from dianhydrides prepared from 4-aminophthalic acid. The present invention provides imide polymers and copolymers having thermoplastic properties at relatively low temperature and having unusually good adhesive properties; and methods for making such polymers and copolymers.

Polymers having imide linkages are generally known in the art. They are characterized by their high tensile strength, toughness, good dielectric properties, and excellent thermal stability. These properties make them particularly well suited for use as self-supporting films, electrical insulating coatings, adhesives, molding and laminating resins, and fibers. But use of these polymers has been limited because of their fabricating and processing characteristics. Fully cured imide polymers had to be heated to relatively high temperatures, approaching degradation temperatures, before they exhibited thermoplastic properties.

Fabrication and processing of imide polymers have also been limited because fully cured imide polymers are generally infusible and insoluble in most solvents. Some of the polymers are capable of high temperature-pressure molding by a powder-sintering process and some are capable of being spun into fibers from strong acid solvents, but the application of such methods are extremely limited. The most useful method of fabricating has been to form the final product to the shape desired from an intermediate before fully curing the imide polymer.

Coatings, fibers and articles of imide polymers have heretofore been made by reacting, in stoichiometric amounts, an aromatic dianhydride with an aromatic diamine. The reaction product is a polyamide-acid soluble in selected solvents and may be removed therefrom by evaporation or diffusion. Selected solvents found to be preferable are N,N'-dimethylformamide, N,N'-dimethylacetamide or N-methylpyrrolidine. Other solvents typical of this selected class include: diethylformamide, N,N'-diethylacetamide, N,N'-dimethylmethoxy acetamide, N-methyl caprolactam, dimethylsulfoxide, tetramethylene urea, pyridine, dimethylsulfone, hexamethylphosphoramide, tetramethylene sulfone, methanamide, N-methylformamide, butyrolactone and N-acetyl-2-pyrrolidone. These solvents can also be used in combination with other solvents such as benzene, xylene, toluene, dioxane and cyclohexane, or used in admixture with each other. These solvents provide a solution polymerization media for the synthesis of polyamide-acid and for forming a desired shape or coating. The solution of polyamide-acid is then dehydrated and cured by the use of heat and, in some instances, a chemical dehydrating unit such as acetic anhydride. The utilization of a chemical dehydrating agent is generaly not employed; in certain molding operations, however, it has been found that a dehydrating agent is useful to precipitate a polyimide from solution.

In the solvent fabrication method volatile by-products such as water as well as solvent are eliminated during the cure. This elimination can create problems which are difficult to overcome; for example, the elimination of water can create voids and cracks in the cured polymer, or a powder polymer cannot be obtained because extensive hydrolysis occurs before the water can escape from the heated, thick layer-solution.

Further, imide polymers and particularly their precursors generally have poor adhesive properties at high temperatures. When the precursors are heated to curing temperature, any of the bonding properties have usually been lost.

The present invention is directed to overcome the problems associated with polyamide fabrication as well as to provide unique imide polymers. The imide polymers of the present invention display bonding and fabricating properties not otherwise found in polyimides.

We provide a polymer containing imide linkages prepared from a dianhydride monomer containing imide linkages and a diamine. Preferably, the dianhydride monomer is prepared by reacting 4-aminophthalic acid with an aromatic dianhydride or an equivalent compound and, thereafter, dehydrating the reaction product by the use of heat and/or a suitable dehydrating agent such as acetic anhydride. the dianhydride monomer is then reacted with an aromatic diamine, and possibly another dianhydride such as 3,4:3',4'-benzophenonetetracarboxylic dianhydride, in a solution to form a polyamide-acid solution. The polyamide-acid is then cured by heating and possibly a convenient chemical dehydrating agent such as acetic anhydride to form a polymer containing imide linkages.

Any dianhydride containing two cyclic anhydride groups is suitable for use in making the dianhydride monomer having imide linkages. Both five and six membered anhydride rings are useful. Dianhydrides known to be particularly suitable are: 2,3:6,7-naphthalene-tetracarboxylic dianhydride. 1,8:4,5-naphthalenetetracarboxylic dianhydride, 3,4:3',4'-diphenyltetracarboxylic dianhydride, 2,3:2',3'-diphenyltetracarboxylic dianhydride, bis (3,4-dicarboxyphenyl) methane dianhydride, 2,2-bis (3,4-dicarboxyphenyl) propane dianhydride, bis (3,4-dicarboxyphenyl) sulfone dianhydride, and bis(3,4-dicarboxyphenyl) ether dianhydride. Other dianhydrides contemplated to be suited are: 1,2:4,5-naphthalenetetracarboxylic dianhydride, 1,8:3,4-naphthalenetetracarboxylic dianhydride, 1,1-bis(3,4-dicarboxyphenyl) ethane dianhydride, 2,2-bis(2,3-dicarboxyphenyl) propane dianhydride, 1,2:3,4-cyclopentanetetracarboxylic dianhydride, 1,2:5,6-hexanetetracarboxylic dianhydride and tetrahydrofurane-2,3:4,5-tetracarboxylicdianhydride, 1,1-bis(2,3-dicarboxyphenyl) ethane dianhydide, bis(2,3-dicarboxyphenyl) methane dianhydride, pyrazine-2,3:5,6-tetracarboxylic dianhydride, thiophene-2,3:4,5-tetracarboxylic dianhydride, and 1,2:3,4-benzenetetracarboxylic dianhydride (mellophanic dianhydride). These various dianhydrides can also be used in mixture with each other. We prefer, however, that 1,2:4,5 benzenetetracarboxylic dianhydride (PMDA) or 3,4:3',4'-benzophenonetetracarboxylic dianhydride (BTDA), and most preferably the latter be the aromatic anhydride used.

Other equivalent compounds may be substituted in whole or in part for the dianhydride.. Especially useful compounds of this class are those containing two ortho-chlorocarbonyl ester groups, or one such group and one anhydride group. Examples are: 2,5bis (carbomethoxy) terephthaloyl chloride, 4,6-bis(carbobutoxy) isophthaloyl chloride, 4,4'-bis(carboethoxy)-3,3'-benzophenone -bis(carbonyl chloride), 1,4,5,8-naphthalenetetracarboxylic-1,8-anhydride-4-methyl ester- 5-acyl chloride, and 2,4-di(carbophenoxy)-1,3-cyclopentane dicarboxylic acid chloride. Other halogens can be substituted for the chlorine in these compounds.

The aromatic diamine preferred for use in the present invention is 4,4'-diaminodiphenyl ether (DAPE). Aromatic diamines also found to be particularly suitable for use in this invention include: 1,3-diaminobenzene (MPD), 4,4'-diaminodiphenylmethane (MDA) 3,4'-diaminobenzanilide (MADPPD), 1,4-diminobenzene, 4,4'-diaminodiphenyl sulfide, 2,2-bis(4-aminophenyl) propane, 1,4-diaminonaphthalene, 4,4'diaminodiphenyl, and 3,3'-dichloro- 4,4' diaminodiphenyl (benzidine). Other aromatic diamines contemplated to be suited are: 4,4'-diaminodiphenyl amine, 4,4-diaminodiphenyl N-methyl amino, 4,4' di- aminodiphenyl N-phenyl amine, 3,3'-diaminodiphenyl sulfone, 4,4'-diaminodiphenyl sulfone, 4,4'-diaminodiphenyl diethylsilane and 4,4'-diaminodiphenyl diphenylsilane. These various aromatic diamines can also be used in mixture with each other.

In the preparation of the dianhydride monomer of the present invention, preferably two moles of 4-aminophthalic acid are reacted with a mole of dianhydride. Yields of approximately 85% have been obtained from such stoichiometric reaction. While variations from the stoichiometric amounts are possible, yield of the monomer will normally be lower because of the resulting separation difficulties. Moreover, an excess of the 4-aminophthalic acid gives rise to the problems inherent in a presence of excess mono-functional material, e.g. reduction in molecular weight of the final polymer. And an excess of the dianhydride will usually decrease the number of internal imide linkages formed in the dianhydride monomer. Accordingly, we prefer that the ratio of 4-aminophthalic acid to dianhydride be as near 2:1 as practical to provide optimum results.

We have found that in following the usual procedure for preparing polyamic-acid solution of the present invention a phenomena of "gel" formation occurs. This gellation may be due to the formation of isoimide linkages causing cross-linking*, or alternatively, to an interaction between the polyamide-acid composition and the solvent. The effect of gellation can be reduced and a more stable polyamide-acid solution formed by adding a few percent of mono-functional material (such as an anhydride) to reduce the molecular weight of the polymer. But such addition of material may have adverse effects on the properties of the final polymer. Alternatively, we have found that the gellation problem can be solved and a stable polyamide-acid solution formed by first preparing a solution of diamine and selected solvent, and maintaining the temperature of the solution between 50 and 120°C., preferably at 110°C., during the addition of the dianhydride monomer. Additionally, it has been helpful to add some of the diamine after the addition of the dianhydride monomer. Relatively stable polyamide-acid solutions are obtained by this method. If gellation does occur within a few days, the gel can be broken up by simply heating the solution, without adverse effects to the final polymer. This is illustrated by several examples hereinafter.

Illustrative of the reactions involved in the present invention is the formation of N,N-bis(3,4-dicarboxyphenyl) pyromellitimide dianhydride monomer from 4-aminophthalic acid and 1,2:4,5 benzenetetracarboxylic dianhydride (PMDA) and the formation of an imide polymer from N,N-bis (3,4-dicarboxyphenyl) pyromellitimide dianhydride monomer and 1,3-diaminobenzene (MPD):

*See N. R. Rodrick and P. L. Bhatia, 28 J. Org. Chem. 2018 (1963).

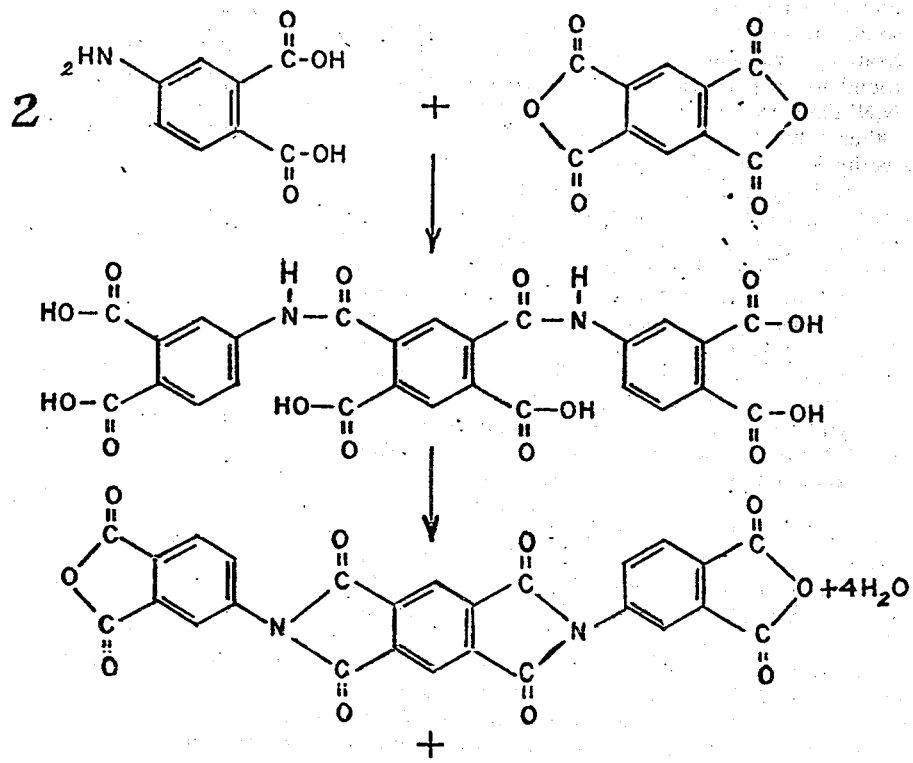

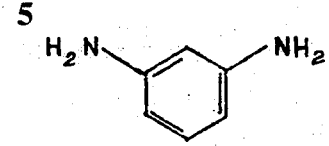

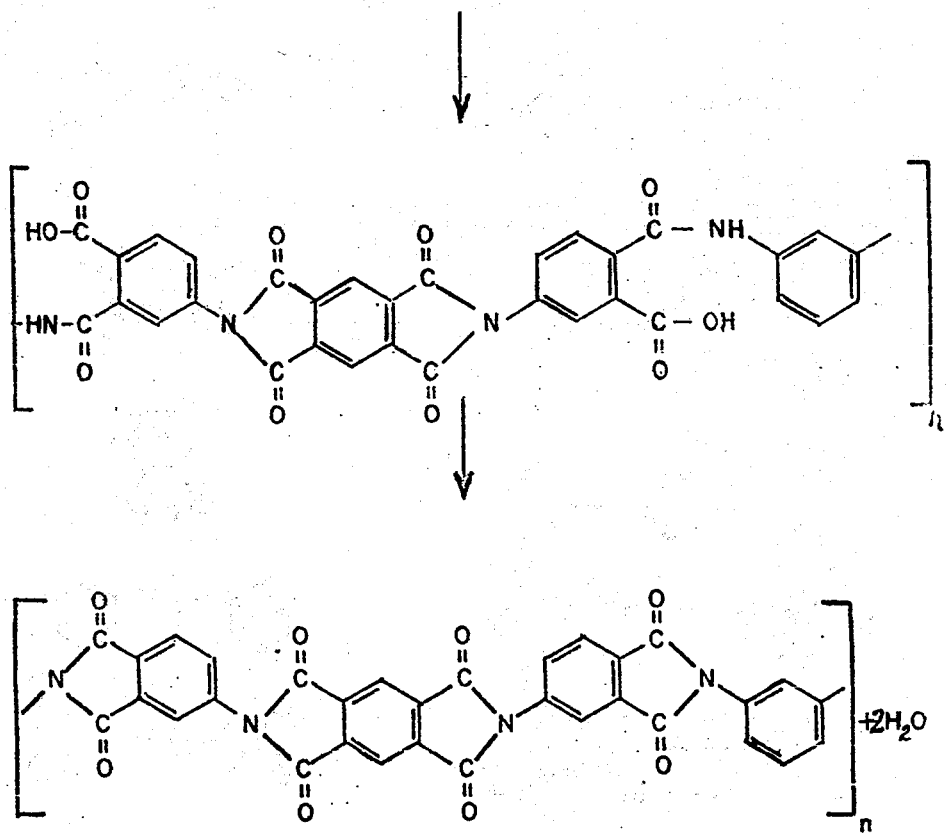

Two moles of 4-aminophthalic acid is condensed with one mole of 1,2:4,5 benzenetetracarboxylic dianhydride (PMDA) to form an amide-acid. The amide-acid is then heated, preferably to about 110°C. in the presence of an excess of a dehydrating agent such as acetic anhydride to form a diimidedianhydride monomer.

A solution of 1,3-diaminobenzene (MPD) and solvent is made and heated. The diimide-dianhydride monomer previously made is thereafter added to form a polyamide-acid solution. The polyamide-acid solution then dehydrated and cured by further heating to form an imide polymer.

The reason for the unique properties of the present invention, e.g. thermoplasticity in the 275°–300°C. range, is not fully understood. It is believed that in large measure the properties derive from the fact that imide linkages are present in the dianhydride. This in turn results in the presence of more imide linkages in the polyamic-acid solution and less volatile by-product to eliminate in the final cure.

The diimide-dianhydride monomers of this invention may also be described as having the following structural formula:

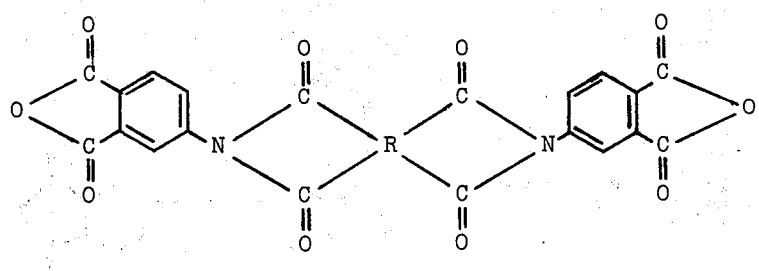

wherein R is a tetravalent radical derived from the particular dianhydride reacted with the 4-aminophthalic acid. The R radicals provided by the heretofore mentioned suitable dianhydrides or other equivalent compounds are outlined in the following table.

| Dianhydride Name | Dianhydride Structural Formula | R Radical |
|---|---|---|
| (A) 1,2:4,5-benzenetetra-carboxylic dianhydride | 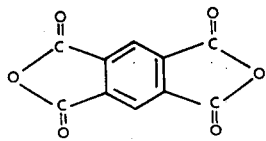 | 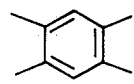 |
| (B) 3,4:3',4'-benzophenone-tetracarboxylic dianhydride | 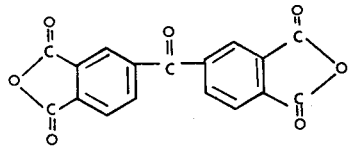 | 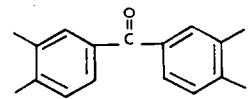 |
| (C) 2,3:6,7-naphthalene-tetra-carboxylic dianhydride | 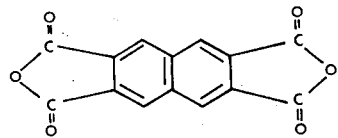 | 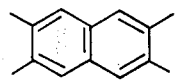 |
| (D) 1,8:4,5-naphthalene tetra-carboxylic dianhydride | 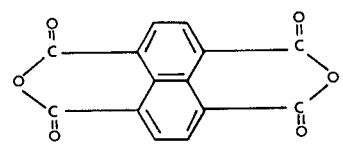 | 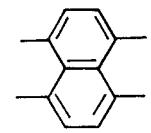 |
| (E) 3,4:3',4'-diphenyltetra-carboxylic dianhydride | 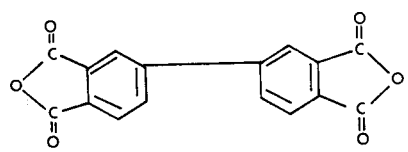 |  |
| (F) 2,3:2',3'-diphenyltetra-carboxylic dianhydride | 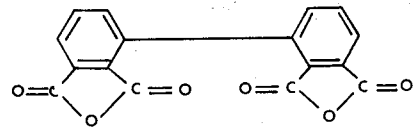 |  |
| (G) bis (3,4-dicarboxyphenyl) methane dianhydride | 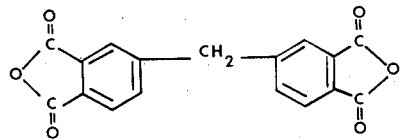 | 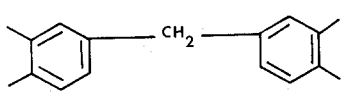 |
| (H) 2,2-bis (3,4-dicarboxyphenyl) propane dianhydride | 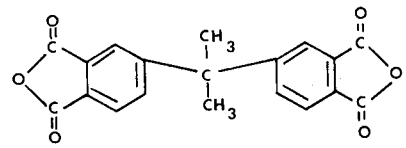 | 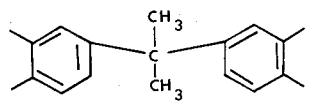 |
| (I) bis (3,4-dicarboxyphenyl) sulfone dianhydride | 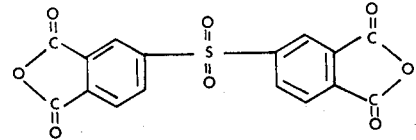 | 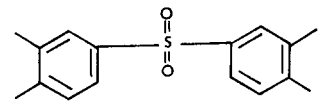 |
| (J) bis (3,4-dicarboxyphenyl) ether dianhydride | 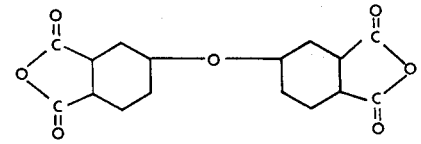 | 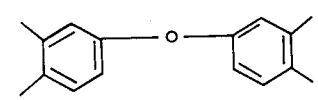 |
| (K) 1,2:4 5-naphthalenetetra-carboxylic dianhydride | 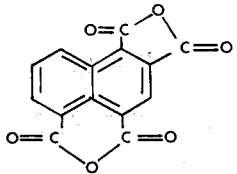 | 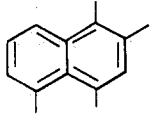 |

| Dianhydride Name | Dianhydride Structural Formula | R Radical |
|---|---|---|
| (L) 1,1-bis (3,4-dicarboxy-phenyl) ethane dianhydride | 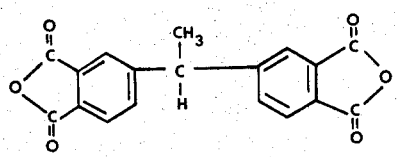 | 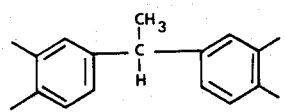 |
| (M) 2,2-bis (2,3-dicarboxy-phenyl) propane dianhydride | 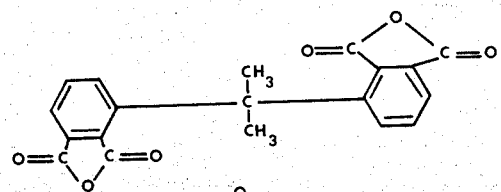 | 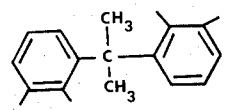 |
| (N) 1,2:3,4 cyclopentane-tetracarboxylic dianhydride | 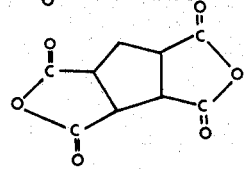 | 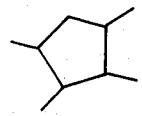 |
| (O) 1,2:4,5-cyclohexane tetracarboxylic dianhydride | 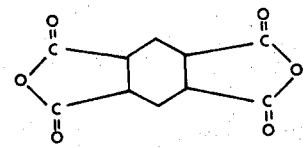 | 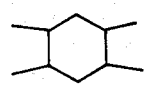 |
| (P) 2,3:4,5-tetrahydro-furan tetracarboxilic dianhydride | 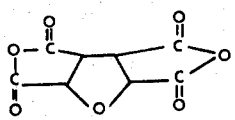 | 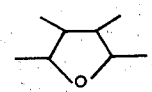 |
| (Q) 1,1-bis(2,3-dicarboxyphenyl) ethane dianhydride | 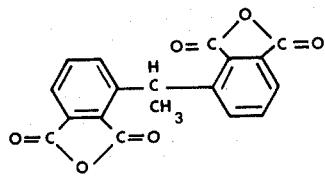 | 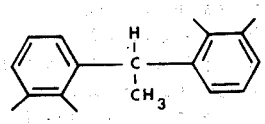 |
| (R) bis (2,3-dicarboxyphenyl) methane dianhydride | 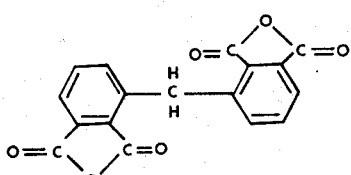 | 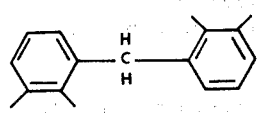 |
| (S) 2,3:5,6-Pyrazine tetracarboxylic dianhydride | 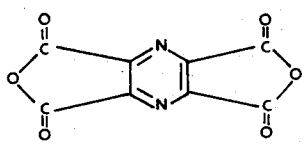 | 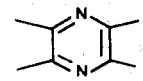 |
| (T) 2,3:4,5-thiophene tetracarboxylic dianhydride | 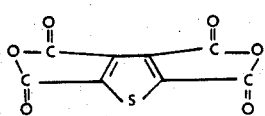 | 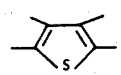 |
| (U) 1,2,:3,4-benzene-tetracarboxylic dianhydride | 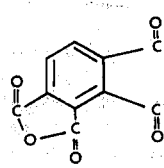 | 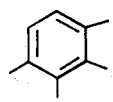 |

It should be apparent that the (B), (G), (H), (I), (J) and (L) tetravalent radicals may be more conveniently described as

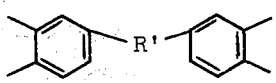

wherein R' is a carbonyl, sulfonyl, oxy or alkylene of up to 3 carbons. Similarly, the (M), (Q) and (R) may be more conveniently described as

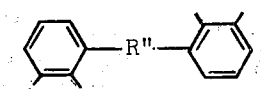

wherein R'' is a alkylene of up to 3 carbons.

Various linkages other than imide linkages can be incorporated into the polymer chains. This can be accomplished by mixing other difunctional and polyfunctional compounds containing the desired linkage or precursors thereof into the polyamide-acid solution, or by using diamines and/or dianhydrides containing the desired linkage. Various suitable vinyl compounds, polyols, polyacids, polyamides, polyesters, polyurethanes, epoxies and the like are possible. However, it is understood that not all compounds within these broad classes are totally compatable. Also, inclusion of some of these compounds may compromise properties of the polyimides for other properties. For example, inclusion of certain vinyl compounds may compromise the property of excellent thermal stability of the polyimides for ease of fabricating capabilities.

Other details, objects and advantages of our invention will be apparent from the following non-limited examples and the tabulations that follow. The tables summarize in convenient form many of the surprising characteristics of our new polymeric system. Not only have we gone a long way towards obviating the fabrication problems, but we have provided a polymer with surprising bonding strength. These advantages are apparent from the tables utilizing the polymers of the subsequent examples in which:

Examples 1 and 2 describe the preparation of dianhydride monomers and the other Examples describe the preparation of imide polymers using the dianhydride monomers of Examples 1 and 2.

EXAMPLE 1

Preparation of a dianhydride from 4-amino-phthalic acid and 1,2:4,5 benzenetetracarboxylic dianhydride A mixture of 362 g. of 4-aminophthalic acid, 1000 g. of N,N'-dimethylacetamide, and 500 g. of dioxane were stirred until almost all the acid was dissolved. To this mixture was added 218 g. of 1,2:4,5 benzenetetracarboxylic dianhydride (PMDA). This mixture was warmed to 90°C. and stirred, and subsequently cooled to 60°C. 10 ml. of pyridine, followed by one liter of acetic anhydride were added. After about five minutes, the formation of a precipitate stopped the stirrer. The mixture was warmed to 108°C. for two hours and then allowed to cool overnight. The solid dianhydride was collected on a filter and dried in a vacuum. Yield was 427 g.

EXAMPLE 2

Preparation of a dianhydride from 4-amino-phthalic acid and 3,4:3',4'-benzophenonetetracarboxylic dianhydride A solution was prepared from 90.5 g. of 4-aminophthalic acid and 500 ml. of N,N'-dimethylacetamide. To this solution was added 80.5 g. of 3,4:3',4'-benzophenonetetracarboxylic dianhydride (BTDA). After stirring for 30 minutes, 220 ml. of acetic anhydride was added. The solution was warmed slowly to 90°C. where a precipitate formed. This mixture was heated to 100°C., held at 100°C. for 90 minutes, and then allowed to cool. The solid dianhydride was collected on a filter, washed with acetic anhydride, and then dried in a vacuum desiccator overnight. It was dried additionally at 200°, 250° and 300°C. a total of three hours. Yield was 124 g., m.p. 315°–319°C.

EXAMPLE 3

Preparation of Polymer from the dianhydride of Example 1 and 4,4'-diaminophenyl ether.

A solution was prepared from 2.0 g. of 4,4'-diaminophenyl ether (DAPE) and 24 g. N,N'-dimethylacetamide. To this solution was added 4.08 g. of solid dianhydride of Example 1. The dianhydride did not dissolve readily so 16 g. more of N,N'-dimethylacetamide was added. The solution gelled.

EXAMPLE 4

Preparation of Polymer from the dianhydride of Example 1, 4,4'-diaminophenyl ether and 3,4:3', 4' benzophenonetetracarboxylic dianhydride A solution was prepared from 4.00 g. of 4,4'-diaminophenyl ether (DAPE), 3.22 g. of 3,4:3',4'-benzophenonetetracarboxylic dianhydride (BTDA) and 100 g. of N,N'-dimethylacetamide. To this solution, was added 4.08 g. of the dianhydride of Example 1. The solution was initially very thin. A flexible film was prepared from the solution. The solution gelled after 3 days of storage in a refrigerator at about 5°C.

EXAMPLE 5

Preparation of Polymer from the dianhydride of Example 2, 4,4'-diaminophenyl ether and 3,4:3',4'-benzophenonetetracarboxylic dianhydride A solution was prepared from 19.8 g. of 4,4'-diaminophenyl ether (DAPE), 16.1 g. of 3,4:3',4'-benzophenonetetracarboxylic dianhydride (BTDA), 0.3 g. of p-aminoacetamide (a monofunctional amine) and 446 g. of N,N'-dimethylacetamide. To this solution was added 30.6 g. of the dianhydride of Example 2. A sample of this solution was placed in a viscometer which was placed in a constant temperature bath set at 35°C. The initial viscosity of the solution was 676 centistokes. After 13 days the viscosity peaked at 7340 centistokes. After an additional 20 days the viscosity dropped to 2760 centistokes. A film cast from the original solution was tough and flexible.

EXAMPLE 6

Preparation of Polymer from the dianhydride of Example 3 and 4,4'-diaminophenyl ether A solution was prepared from 2.00 g. of 4,4'-diaminophenyl ether (DAPE) and 40 g. of N,N'-dimethylacetamide. To this solution was added 6.36 g. of the dianhydride of Example 2 and later 10 g. more of N,N'-dimethylacetamide. A sample of the solution was placed in a viscometer which was placed in a constant-temperature bath set at 35°C. The initial viscosity was 1160 centistokes. After 3 days the viscosity was 7940 centistokes. After 8 days the viscosity peaked at 19,400 centistokes. And after 14 days the viscosity declined to 15,700 centistokes. A film cast from the original solution was tough and flexible.

EXAMPLE 7

Preparation of Polymer from the dianhydride of Example 1, 4,4'-diaminophenyl ether and 3,4:3',4'-benzophenonetetracarboxylic dianhydride In a 500 ml. flask equipped with a stirrer, thermometer and heating mantle, a solution was prepared with 245 g. of N,N'-dimethylacetamide and 15 (.075 mole) of 4,4'-diaminophenyl ether (DAPE). To this solution was added successively over 20 minutes 0.1 ml. of trifluoroacetic anhydride, 17.71 g. (0.055 mole) of 3,4:3',4'-benzophenonetetracarboxylic dianhydride (BTDA) and 25.4 (0.05 mole) of the dianhydride of Example 1. The solution at the same time was being heated; the temperature after another 20 minutes rose to 90°C. The addition of 5 g. (0.025 mole) of 4,4'-diaminodiphenyl ether raised the temperature from 90° to 93°C. The temperature was kept at 88° to 98° for 90 minutes and 53 g. of N,N'-dimethylacetamide was added. This gave a product with viscosity at Z—Z on the Gardner Scale, that decreased to Z-1 on standing overnight.

EXAMPLE 8

Preparation of Polymer from the anhydride in Example 1, 4,4'-diaminophenyl ether and 3,4:3',4'-benzophenonetetracarboxylic dianhydride A solution was prepared from 20 g. (0.1 mole) of 4,4'-diaminophenyl ether (DAPE) and 230 g. of N,N'-dimethylacetamide. To the solution was stirred in 25.44 g. (0.079 mole) of 3,4:3',4'-benzophenonetetracarboxylic dianhydride (BTDA). The temperature during this addition rose spontaneously to 37°C. Over a period of 10 minutes the temperature was raised to 55°C. and 12.72 g. (0.025 mole) of the dianhydride of Example 1 was stirred into the solution. About a 4% excess of said dianhydride was used because of estimated impurities in the 3,4:3',4'-benzophenonetetracarboxylic dianhydride (BTDA), assumed to be mostly tetra acid. The solution became very viscous and the temperature was raised to 95°C. and held there for 30 minutes. On cooling the solution had a Gardner viscosity of Z and contained 17.2% solids.

EXAMPLE 9

Preparation of Polymer from the dianhydride of Example 1, 4,4'-diaminophenyl ether and 3,4:3',4'-benzophenonetetracarboxylic dianhydride In a 500 ml. flask equipped with stirrer, thermometer, and heating mantle, a solution was prepared with 216 g. N,N'-dimethylacetamide and 19.5 g. (0.0975 mole) of 4,4'-diaminodiphenyl ether (DAPE). The solution was warmed and 6.35 g. (0.0125 mole) of the dianhydride from Example 1 was added. The solution was very viscous and was kept at 91° for 3 hours.

EXAMPLE 10

Preparation of Polymer from the dianhydride of Example 1, 4,4'-diaminophenyl ether and 4,4'-diaminodiphenylmethane In a 500 ml. flask equipped with stirrer, thermometer, and heating mantle, a solution was prepared with 250 g. N,N'-dimethyl acetamide and 19.8 g. (0.1 mole) of 4,4'-diaminophenylmethane. To this solution was added 17.5 g. (0.0545 mole) of 3,4:3',4'-benzophenonetetracarboxylic dianhydride (BTDA) and the temperature rose to 38°C. The solution was further warmed to 80°C., followed by the addition of 25.4 g. (0.05 mole) of the dianhydride of Example 1. The viscous solution was then warmed to 112°C. and allowed to cool slowly. Viscosity on cooling was Z-5 on the Gardner Scale.

EXAMPLE 11

Preparation of Polymer from the dianhydride of Example 1, 4,4'-diaminophenyl ether 4,4'-diaminodiphenylmethane, 1,3-diaminobenzene, and 3,4:3',4'-benzophenonetetracarboxylic dianhydride In a 500 ml. flask equipped with stirrer, thermometer, and heating mantle, a solution was prepared with 255 g. of N,N'-dimethyl acetamide, 9.9 g. (0.05 mole) of 4,4'-diaminodiphenylmethane (MDA), and 2.7 g. (0.025 mole) of 1,3-diaminobenzene (MPD). To this solution 17.5 g. (0.0545 mole) of 3,4:3',4'-benzophenonetetracarboxylic dianhydride (BTDA) was added. The solution was heated to 70°C. and 25.4 g. (0.05 mole) of the dianhydride from Example 1 was added. The solution was further warmed to 90°C. and another 2.7 g. (0.025 mole) of 1,3-diaminobenzene (MPD) was added. After 150 minutes at 90°C. the solution had a viscosity of Z-2 on the Gardner Scale.

EXAMPLE 12

Preparation of Polymer from the dianhydride of Example 1, 4,4'-diaminophenyl ether and 1,2:4,5 benzenetetracarboxylic dianhydride In a 500 ml. flask equipped with a stirrer, thermometer, and heating mantle, a solution was prepared with 230 g. N,N'-dimethylacetamide and 15 g. (0.075 mole) of 4,4'-diaminodiphenyl ether (DAPE). To this solution 12 g. (0.055 mole) of 1,2:4,5-benzenetetracarboxylic dianhydride (BTDA) was added. The solution was warmed to 50°C., and 25.5 g. (0.05 mole) of the dianhydride of Example 1 was added. The solution was warmed to 85°C. and 5 g. (0.025 mole) more of 4,4'-diaminodiphenyl ether (DAPE) was added and later 57 g. of N,N'-dimethylacetamide. The solution had a viscosity of Z-2 on the Gardner Scale.

EXAMPLE 13

Preparation of Polymer from the dianhydride of Example 1 and 4,4'-diaminophenyl ether In a 500 ml. flask equipped with a stirrer, thermometer, and heating mantle, a solution was prepared with 245 g. of N,N'-dimethylacetamide and 53.4 g. (0.105 mole) of the dianhydride of Example 1. The solution was warmed to 108°C. and 19 g. (0.095 mole) of 4,4'-diaminodiphenyl ether (DAPE) was added over 47 minutes as the solution was allowed to cool. An additional 100 g. N,N'-dimethylacetamide and 0.5 g. (0.0025 mole) of 4,4'-diaminodiphenyl ether (DAPE) were added. The solution was left overnight and became somewhat more viscous. At this point an additional 0.1 g. (.0005 mole) of 4,4'-diaminodiphenyl ether (DAPE) and 40 g. of N,N'-dimethylacetamide were added.

EXAMPLE 14

Preparation of Polymer from the dianhydride of Example 1, 4,4'-diaminophenyl ether, 1.3-diaminobenzene, and 3,4:3',4'-benzophenonetetracarboxylic dianhydride In a 500 ml. flask equipped with a stirrer, thermometer, and heating mantle, a solution was prepared with 250 g. of N,N'-dimethylacetamide, 15 g. (0.075 mole) of 4,4'-diaminodiphenyl ether (DAPE), and 2.7 g. (0.025 mole) of 1,3-diaminobenzene (MPD). To the cold solution 25.4 g. (0.079 mole) 3,4:3',4'-benzophenonetetracarboxylic dianhydride (BTDA) was added. The solution was warmed to 89°C. and 12.7 g. (0.025 mole) of the dianhydride of Example 1 was added. The solution was kept above 90° for 90 minutes and then allowed to cool.

EXAMPLE 15

Preparation of Polymer from the dianhydride of Example 1, 4,4' diaminophenyl ether, 1,3-diaminobenzene, and 3,4:3',4'-benzophenonetetracarboxylic dianhydride In a 500 ml. flask equipped with a stirrer, thermometer, and heating mantle, a solution was prepared with 223 g. of N,N'-dimethylacetamide, 12 g. (0.06 mole) of 4,4'-diaminodiphenyl ether (DAPE), and 4.24 g. (0.04 mole) 1,3-diaminobenzene (MPD). To this unheated solution 27.1 g. (0.084 mole) 3,4:3',4'-benzophenonetetracarboxylic dianhydride (BTDA) was added. The solution was warmed to 81°C. and 10.16 g. (0.02 mole) of the dianhydride of Example 1 was added. The temperature was kept at 89° to 102°C. for about 20 minutes.

EXAMPLE 16

Preparation of Polymer from the dianhydride of Example 2, 4,4'-diaminophenyl ether and 1,2:4,5-benzenetetracarboxylic dianhydride In a 500 ml. flask equipped with a stirrer, thermometer, and heating mantle, a solution was prepared with 245 g. of N,N'-dimethylacetamide and 20 g. (0.1 mole) of 4,4'-diaminodiphenyl ether (DAPE). To this solution was added 10.9 g. (0.05 mole) of 1,2:4,5-benzenetetracarboxylic dianhydride PMDA), followed by 0.1 ml. of trifluoroacetic anhydride. As the solution was warmed, 30.6 g. (0.05 mole) of the dianhydride of Example 2 was added. An additional 100 g. N,N'-dimethylacetamide was added as the solution was warmed to 112°C. over a 90 minute period. This material had a viscosity of Z on the Gardner Scale rising to Z-5 after setting overnight. The solution was warmed to 95°C. for about 20 minutes and on cooling the viscosity had decreased to between Y and Z.

EXAMPLE 17

Preparation of Polymer from the dianhydride of Example 2, 4,4'-diaminophenyl ether and 3,4:3',4'-benzophenonetetracarboxylic dianhydride In a 500 ml. flask equipped with a stirrer, thermometer, and heating mantle, a solution was prepared from 373 g. of N,N'-dimethylacetamide and 15 g. (0.075 mole) of 4,4'-diaminodiphenyl ether (DAPE). First 17.71 g. (0.055 mole) 3,4:3',4'-benzephenonetetracarboxylic dianhydride (BTDA) was added. Then after heating the solution to 80°C., 30.6 g. (0.05 mole) of the dianhydride of Example 2 was added. After 20 minutes the temperature had been increased to 100°C. and 5 g. (0.025 mole) of 4,4'-diaminodiphenyl ether (DAPE) was added. After cooling the solution had a viscosiy between U and V on the Gardner Scale.

EXAMPLE 18

Preparation of Polymer from the dianhydride of Example 2, 4,4'-diaminophenyl ether and 3,4:3',4'-benzophenonetetracarboxylic dianhydride In a 500 ml. flask equipped with a stirrer, thermometer, and heating mantle, a solution was prepared from 252 g. of N,N'-dimethylacetamide and 20 g. (0.1 mole) 4,4'-diaminodiphenyl ether (DAPE). To the solution was added 20.4 g. (0.033 mole) of the dianhydride of Example 2 and 21.5 g. (0.067 mole) of 3,4:3',4'-benzophenonetetracarboxylic dianhydride (BTDA). The solution was then diluted with 180 g. N,N'-dimethylacetamide to a calculated 12.8% solid. The viscosity was 1236 centistokes.

EXAMPLE 19

Preparation of Polymer from the dianhydride of Example 1, 4,4'-diaminophenyl ether and 3,4:3',4'-benzophenonetetracarboxylic dianhydride In a 500 ml. flask equipped with a stirrer, thermometer, and heating mantle, a solution was prepared from 236 g. of N,N'-dimethylacetamide and 19.5 g. (0.0975 mole) of 4,4'-diaminodiphenyl ether (DAPE). To this solution was first added 24.5 g. (0.076 mole) 3,4:3',4'-benzophenonetetracarboxylic dianhydride (BTDA). Then after warming the solution to 95°C., 15.3 g. (0.025 mole) of the dianhydride of Example 2 was added. The solution was kept warm for about 3 hours before cooling.

EXAMPLE 20

Preparation of Polymer from the dianhydride of Example 2, 4,4'-diaminophenyl ether and 3,4:3',4'-benzophenonetetracarboxylic dianhydride In a 500 ml. flask equipped with a stirrer, thermometer, and heating mantle, a solution was prepared from 220 g. of N,N,-dimethylacetamide and 19.5 g. (0.0975 mole) of 4,4'-diaminodiphenyl ether (DAPE). To this solution was added 28.2 g. (0.0875 mole) of 3,4:3',4'-benzophenonetetracarboxylic dianhydride (BTDA). Then after warming to 80°C., 7.65 g. (0.0125 mole) of the dianhydride of Example 2 was added. This was kept warm for 2 to 3 hours and then cooled. This solution had a viscosity of Z-5 on the Gardner Scale. 30 g. N,N'-dimethylacetamide was subsequently added.

EXAMPLE 21

Preparation of Polymer from the dianhydride of Example 2 and 4,4'-diaminophenyl ether In a 500 ml. flask equipped with a stirrer, thermometer, and heating mantle, a slurry was prepared with 168 g. N,N'-dimethylacetamido and 32.13 g. (0.0525 mole) of the dianhydride of Example 2. Over a 40 minute period 10 g. (0.05 mole) of 4,4'-diaminodiphenyl ether (DAPE) was added. The temperature reached 80°C. and was allowed to cool to 60°C. over a 3 hour period. To the solution 50 g. of N,N'-dimethylacetamide together with 0.1 g. of p-aminobenzoic acid was added. After setting overnight the viscosity of the solution was Z-4 on the Gardner Scale.

EXAMPLE 22

Preparation of Polymer from the dianhydride of Example 2, 1,3-diaminobenzene and 3,4:3',4'-benzophenonetetracarboxylic dianhydride In a 500 ml. flask equipped with a stirrer, thermometer, and a heating mantle, a solution was prepared from 228 g. of N,N'-dimethylacetamide and 8 g. (0.074 mole) of 1,3-diaminobenzene (MPD). To this solution was added first 16.1 g. (0.05 mole) 3,4:3',4'-benzophenonetetracarboxylic dianhydride (BTDA). Then after warming to 70°C., 30.6 g. (0.05 mole) of the dianhydride of Example 2 was added. About 40 minutes later an additional 2.5 g. (0.023 mole) 1,3-diaminobenzene (MPD) was added.

EXAMPLE 23

Preparation of Polymer from the dianhydride of Example 2, and 4,4'-diamino-diphenylmethane In a 500 ml. flask equipped with stirrer, thermometer, and heating mantle, a slurry was prepared with 166 g. of N,N'-dimethylacetamide and 32.1 g. (0.0525 mole) of dianhydride of Example 2. The slurry was warmed to 70° and a total of 10.1 g. (0.051 mole) 4,4'-diaminodiphenylmethane (MDA) was added in portions over a 5 hour period.

EXAMPLE 24 Preparation of Polymer from the dianhydride of Example 2, 4,4'-diaminodiphenylmethane In a 500 ml. flask equipped with a stirrer, thermometer, and heating mantle, a solution was prepared from 266 g. of N,N'-dimethylacetamide and 15 g. (0.076 mole) of 4,4'-diaminodiphenylmethane (MDA). To this solution at first was added 17.4 g. (0.054 mole) of 3,4:3',4'-benzophenonetetracarboxylic dianhydride (BTDA). Then 30.6 g. (0.05 mole) of the dianhydride of Example 2 was added as the temperature was raised to 88°C. A further 4.8 g. (0.0242 mole) 4,4'-diaminodiphenylmethane (MDA) was added over a 5 hour period.

EXAMPLE 25

Preparation of Polymer from the dianhydride of Example 2, 4,4'-diaminodiphenylmethane In a 500 ml. flask equipped with a stirrer, thermometer, and heating mantle, a solution was prepared from 237 g. of N,N'-dimethylacetamide and 15 g. (0.076 mole) of 4,4'-diaminodiphenylmethane (MDA). To this solution was added first 25.12 g. (0.078 mole) and then 15.3 g. (0.025 mole) of the dianhydride of Example 2, as the temperature was raised to 68°. An additional 4.8 g. (0.024 mole) 4,4'-diaminodiphenylmethane (MDA) was added over a 5 hour period.

EXAMPLE 26

Preparation of Polymer from the dianhydride of Example 1, 4,4'-diaminodiphenylmethane and 3,4:3',4'-benzophenonetetracarboxylic dianhydride The solution was formed from 15 g. of 4,4'-diaminodiphenylmethane (MDA) and 244 g. of N,N'-dimethylacetamide. To the solution was stirred in 16.1 g. of 3,4:3',4'-benzophenonetetracarboxylic dianhydride (BTDA). The solution at the time of this addition was 37°C. The solution was then heated to about 70°C. and 25.4 g. of the dianhydride of Example 1 was added. The solution continued to be stirred and heated to between 55°C. and 95°C. for about 5 hours. During this 5 hour period, more particularly at the end of the second hour, 4.3 g. more of 4,4'-diaminodiphenylmethane (MDA) was added. The solution after standing overnight was gelled. The gel was broken up by an additional heating. A film cast from the solution was tough and flexible.

EXAMPLE 27

Preparation of Polymer from the dianhydride of Examples 1, 4,4'-diaminodiphenyl ether and 3,4:3',4'-benzophenonetetracarboxylic dianhydride 70 g. of 4,4'-diaminodiphenyl ether (DAPE) and 920 g. of N,N'-dimethylacetamide were stirred together and heated to form a solution. To the solution was added 99 g. of 3,4:3',4'-benzophenonetetracarboxylic dianhydride (BTDA). The solution at the time of addition was 46°C. The solution was further heated to about 70°C. and 50.8 g. of solid dianhydride of Example 1 was added to the solution. The solution was further heated for about 2 hours at about 90°C. During the two hours of heating, 10 g. more of 4,4'-diaminodiphenyl ether (DAPE) was added in 2 batches of 5 g. each.

Two strips of glass fiber cloth were dipped into the solution, and thereafter air dried for 40 minutes. The two strips of glass cloth were warmed in an oven to 87°C. and then allowed to cool. The two strips of dipped cloth were thereafter baked out for two hours at 175°C. The build up of resin on the glass cloth was about 43%.

EXAMPLE 28

Preparation of Polymer from the dianhydride of Examples 2, 1,3-diaminobenzene and 1, 2:45-benzenetetracarboxylic dianhydride A solution prepared from 10.8 g. (0.1 mole) of 1,3-diaminobenzene (MPD) and 245 g. of N,N'-dimethylacetamide. To the solution was added 10.9 g. of 1,2:4,5-benzenetetracarboxylic dianhydride (PMDA) and 0.1 ml. (0.00176 mole) of trifloroacetic anhydride. Thereafter 30.6 g. of the dianhydride of Example 2 was stirred into the solution and the mixture was warmed at about 70°C. A film was cast from the solution on an aluminum dish and films were cast on glass plates by baking at 150°, 200°,270° and 300°C. respectively. The film cast on the aluminum dish and the film cast on the glass plate and cured at 150°C. were somewhat brittle. The other films cast exhibited good tensile strength and about 5% elongation.

EXAMPLE 29

Preparation of Polymer from the dianhydride of Examples 2 and 4,4'-diaminophenyl ether A solution was prepared from 20 g. of 4,4'-diaminophenyl ether (DAPE) and 325 g. of N,N'-dimethylacetamide. To the solution was stirred in 60.2 g. of the dianhydride of Example 2 over about a 35 minute period. 160 more g. of N,N'-dimethylacetamide was added after about one hour. The dianhydride of Example 2 was not all dissolved and the mixture was very viscous. After a short time the mixture appeared gelled, but 200 g. more of N,N'-dimethylacetamide was stirred in and moderate heat was applied up to bring the solution up to 40°C. After about 2 hours of applying heat the temperature was up to 60°C. After further heating the solution was about 85°C. and the gel broke up. The solution was then allowed to cool. A film cast from the solution was tough and flexible.

EXAMPLE 30

Preparation of Polymer from the dianhydride of Examples 1 and 4,4'-diaminodiphenylmethane 280 g. of N,N'-dimethylacetamide and 53.4 g. of the anhydride of Example 1 were stirred together and warmed. To the slurry was added 15 g. of 4,4'-diaminodiphenylmethane (MDA) over a period of about 30 minutes, during which time the temperature increased from 40°C. to 61°C. The solution was stirred and heated for about 2 hours. At the end of the 2 hour period most of the solid was dissolved. 3 g. more of 4,4'-dimethyldiphenylmethane (MDA) was then added over about the next 35 minutes, during which time the temperature ranged from 84° to 90°C. The solution was further heated for about 5 hours, during which time 1,2 g. more of 4,4'-diaminodiphenylmethane (MDA) was added. The solution was allowed to set overnight and it became very viscous. Next morning 50 g. more of N,N'-dimethylacetamide was added and the solution was further heated at about 90°C. for about 2 hours, during which time an additional 0.2 g. of 4,4'-diaminodiphenylmethane was added (MDA). The solution contained 18% solids and had a viscosity of Z-4 on the Gardner Scale. After sitting for another day the solution apparently gelled. The gelled solution was warmed in an oven to about 90°C. and stirred and thereafter heated to 225°C. where it was a fairly thin cloudy solution.

EXAMPLE 31

Preparation of Polymer from the dianhydride of Example 1 and 3,4'-diaminobenzanilide 300 g. of N,N'-dimethylacetamide and 53.4 g. of the anhydride of Example 1 were stirred together and warmed. To the slurry was added 20 g. of 3,4'-diaminobenzanilide (MAB-PPD) over a period of about one hour, during which time the temperature ranged from 70° to 79°C. The solution was further heated for about 5 hours, during which time an additional 2 g. of 3,4'-diaminobenzanilide (MAB-PPD) were stirred in. 50 g. more of N,N'-dimethylacetamide was thereafter added, and the solution was allowed to sit overnight. The next morning 50 g. more of N,N'-dimethylacetamide was added, and the solution was heated for about 1 ½ hours during which time 0.3 g. of 3,4'-diaminobenzanilide was added. The solution contained 16% solids and had a viscosity of Z-2 on the Gardner Scale.

EXAMPLE 32 preparation of Polymer from the dianhydride of Example 1, 4,4'-diaminophenyl ether, 3,4:3',4'-benzophenonetetracarboxylic dianhydride A solution was prepared from 16 g. (0.08 mole) of 4,4'-diaminophenyl other (DAPE) and 180 g. of N,N'-dimethylacetamide. The solution was warmed to 40°C. and 19.32 g. (0.06 mole) of 3,4:3',4'-benzophenonetetracarboxylic dianhydride (BTDA) was stirred into the solution. The solution was further heated to about 100°C. and 12.24 g. (0.02 mole) of the dianhydride of Example 1 was added. The solution was warmed and stirred at about 100°C. for 30 minutes during which time an additional 100 g. of N,N'-dimethylacetamide anhydride, 30 g. of xylene and 100 ml. of acetic anhydride were added. The solution was cooled to about 80°C. and 1 ml. of pyridine was added. In a few minutes a yellow precipitate began to form; however a large part was lost because of splashing by the stirrer. The mixture was then cooled and the precipitate was collected on a vacuum filter. This filtrate was dried in a vacuum at 180°C. over the weekend. Part of the dried precipitate was cured by heating in an oven (in air) at 325°C. for about 1 hour and part was molded.

EXAMPLE 33

Preparation of conventional polyimides from 3,4:3',4'-benzophenonetetracarboxylic dianhydride and 4,4'-diaminophenyl ether for comparison purposes In a one-liter flask equipped with a stirrer and thermometer, a solution was prepared 475 g. N,N'-dimethylacetamide and 40 g. (0.2 mole) 4,4'-diaminodiphenyl ether (DAPE). To this solution was added 64.4 g. (0.2 mole) 3,4:3',4'-benzophenonetetracarboxylic dianhydride (BTDA) and the solution stirred for one hour.

This polyimide was used for purposes of comparing the properties of the imide polymer of the present invention with a conventional polyimide.

The following test was devised to determine the thermoplastic properties of the imide polymers of various of the above examples. Films of approximately 2 mils in thickness were cast and were cured for about 30 minutes to one hour at 250°C. The time and temperature were arbitrarily chosen to evaluate curability at relatively low temperatures; normally imide polymer films are cured at about 300°C. The films were then cut into one inch strips and clamped at both ends, the clamps being five inches apart. The lower clamp acted as a weight of 7.4 g. and the upper clamp was adapted to be hooked to the roof of an oven. The strips were then placed in a hot oven at 325°C. and the door closed for 5 minutes. The distances between the two clamps were then measured and 5 inches subtracted. The results for the imide polymers tested are given in Table I.

TABLE I

| Composition | Stretch in Inches (of a 5 Inch Specimen) |
|---|---|
| EXAMPLE 7 | 10 5/8 |
| EXAMPLE 8 | 8 5/8 |
| EXAMPLE 9 | 1 1/8 |
| EXAMPLE 10 | 1/2 |
| EXAMPLE 11 | 1/16 |
| EXAMPLE 12 | 1/8 |
| EXAMPLE 13 | 5/8 |
| 1 to 1 blend of EXAMPLES 8 and 10 | 9 |
| EXAMPLE 14 | 8 7/8 |
| EXAMPLE 15 | 0 |
| EXAMPLE 15 (blend) | 0 |
| EXAMPLE 16 | 3/4 |
| EXAMPLE 17 | 10 1/2 |
| EXAMPLE 18 | 3/4 |
| EXAMPLE 19 | 5/8 |
| EXAMPLE 20 | 3/8 |
| EXAMPLE 21 | 2 1/4 |
| EXAMPLE 22 | 1/4 |
| EXAMPLE 23 | 1/2 |
| EXAMPLE 24 | 7/8 |
| EXAMPLE 25 | 1 |
| EXAMPLE 33 | 5/16 |

In accordance with this test, any stretch value of 5 inches or over can be taken as equivalent and an indication of good thermoplastic properties. A stretch of one half inch or less can be taken as equivalent and a showing of poor thermoplastic properties. A stretch greater than ½ inch and less than 4 inches can be regarded as demonstrating marginal thermoplastic properties.

It can be seen from the above table that polymers exhibiting the best thermoplastic properties were copolymers containing 4,4'-diaminophenyl ether as the diamine component and 3,4:3',4'-benzophenonetetracarboxylic dianhydride in addition to the dianhydride containing imide linkages.

The effect of varying the curing temperature on the thermoplastic properties of some of the polymers of the above examples were also investigated. The results of this test are shown in Table II. The procedure and temperature at which the stretching is carried out was the same as in the testing shown in Table I.

TABLE II

| Curing Temp. (C°) | Stretch in Inches (of a 5 Inch Specimen) | | | |
|---|---|---|---|---|
| | Example 33 | Example 26 | Example 27 | 2 to 1 Blend of Ex. 33 and 27 |
| 150 | — | 10 | — | — |
| 175 | 10 | 9 1/8 | 6 3/8 | 9 1/4 |
| 200 | 3/4 | 8 1/2 | 8 3/4 | 2 3/4 |
| 225 | 7/8 | 1 1/2 | 7 1/2 | 1/8 |
| 250 | 5/16 | 3/8 | 6 | 1/8 |
| 275 | — | — | 2 3/8 | — |
| 300 | — | — | 5 5/16 | — |

As seen from Table II, all of the polymers prepared from dianhydride monomers prepared from 4-aminophthalic acid demonstrated much better thermoplastic properties than conventional polyimide when cured at 200°C. The conventional polyimide exhibited thermoplastic properties with the cure of 175°C., but not with 200°C. or more. Of the compositions in Table II only the composition of Example 27 demonstrated appreciable thermoplastic properties after cures of 225°C. and above; these compositions still exhibited good thermoplastic properties after being cured at 300°C.

The composition of Example 27 was also tested to determine the effect of varying curing time on thermoplastic properties. After a cure of 48 hours at 250°C. a strip of this polymer still stretched 6 inches in the stretch test described in connection with Table 1. This was about the same as a sample of the same composition cured for about 15 minutes at 250°C.

The temperature at which the stretching test was carried out was varied to determine the effect on the thermoplastic properties. The results of this test are shown in Table III.

TABLE III

| Composition | Stretch in Inches (of a 5 Inch Specimen) | | |
|---|---|---|---|
| | 275° | 300°C. | 325°C. |
| EXAMPLE 21 [A] | 1/8 | 1 1/4 (1 5/8)* | 1 3/8 (3 1/2) |
| EXAMPLE 21 [B] | 7/8 | 2 1/8 (5 3/8) | 2 1/4 (5 3/8) |
| EXAMPLE 21 [C] | 1/8 | 3 5/8 | 3 5/8 |
| EXAMPLE 21 [D] | 1/8 | 4 3/4 | 4 3/4 |
| EXAMPLE 16 | 0 | 10 1/4 | 10 5/8 |
| EXAMPLE 17 | 6 1/4 | 10 10 1/2 | |

Table III shows that for the polymers tested there was no significant difference between stretching the film at 300°C. and stretching the film at 325°C. In two samples the critical temperature for thermoplasticity is between 275° and 300°C. and for the third sample below 275°C. Because of the marginal stretchability of the compositions of Example 21 different samples were cured at 250° (A and B) and 275°C. (C and D), and different weights were used for different samples (B and D with 14.8 g.; A and C with 7.92 g.). It can be seen from the data in Table III that approximately doubling the weight on these strips increased the stretching by 25 to 70% and raising the curing temperature from 250° to 275°C. increased the stretching by about 100%.

Most of the compositions in the above examples formed films that were tough and strong. The tensile strength and the elongation values of the unstretched films are given for several of the polymers in Table IV.

TABLE IV

| Composition | Top Cure Temp. (°C.) | Tensile Strength (psi) | Elongation (percent) |
|---|---|---|---|
| EXAMPLE 21 | 250 | 26,000 | 6.1 |
| | 325 | 21,000 | 3.5 |
| EXAMPLE 28 | 275 | 25,300 | 6.5 |
| | 300 | 27,800 | 5.8 |
| | 325 | 25,200 | 4.3 |
| EXAMPLE 16 | 250 | 15,300 | 7.1 |
| | 275 | 14,700 | 7.0 |
| | 300 | 17,200 | 9.3 |
| | 325 | 13,400 | 5.2 |
| EXAMPLE 12 | 250 | 17,300 | 5.3 |
| | 325 | 13,100 | 8.0 |
| EXAMPLE 17 | 250 | 17,600 | 4.7 |
| EXAMPLE 23 | 250 | 19,500 | 5.0 |
| | 325 | 17,200 | 4.2 |
| EXAMPLE 19 | 250 | 21,500 | 5.0 |
| EXAMPLE 20 | 250 | 18,000 | 4.9 |
| EXAMPLE 9 | 250 | 17,500 | 5.5 |

The thermal stability of the polymers of the above examples was also tested. The weight loss data at 325°C. for several of the polymers is shown in Table V.

TABLE V

| Composition | Weight Loss (%) Aged 400 Hrs. at 325°C | Weight Loss (%) Aged 800 Hrs. at 325°C |
|---|---|---|
| EXAMPLE 29 | 5.1 | 10 |
| EXAMPLE 8 | 9.2 | 29.6 |
| EXAMPLE 10 | 8.7 | 17.5 |
| EXAMPLE 11 | 5.6 | 10.7 |
| EXAMPLE 30 | 8.5 | 14.6 |
| EXAMPLE 31 | 5.5 | 11.2 |
| BLEND OF EX. 8 and 10 | 6.1 | 15.1 |
| EXAMPLE 23 | 5.3 | 10.5 |
| EXAMPLE 24 | 6.2 | — |
| EXAMPLE 25 | 10.0 | — |
| Polyimide Prepared from BTDA and MPD | 2.3 | 4.1 |
| EXAMPLE 33 | 4.0 | 6.6 |

*Valves in parenthesis are repeated data.

The thermal stability of those polymers shown by Table V are very good but not quite as good as the best conventional polyimides. Weight loss data is, however, very sensitive to impurities and we contemplate that further purification of the dianhydride monomers containing imide linkages will result in better thermal stability.

The compressive strength of the polymers of the above examples were also tested. For this test small pellets were molded from powder at 20,000 psi and 405°C. for two hours. The results for the polymers tested is shown in Table VI.

TABLE VI

| Composition | Compression Strength (psi) |
|---|---|
| EXAMPLE 12 | 32,700 |
| EXAMPLE 8 | 29,900 |
| EXAMPLE 12 | 19,400 |
| Polyimide prepared from BTDA and MPD | 45,000 |

The compressive strengths for the polymers of our invention are considered quite good, although not as good as the compressive strengths of conventional polyimides. We contemplate, however, that variations in formulation of the polymer of our invention will equal conventional polyimides in compressive strength.

The polymer of Example 14 was also tested for its adhesive properties. In this test adhesives were first prepared by partially curing the polymer, usually at 200°C., to remove most of the solvent (commonly called "B" stage curing). The adhesives were then applied between various substrates and films further cured at various temperatures and pressures. The results of these tests are set forth in Table VII and Table VIII.

Specific test procedures and parameters for these tests were as follows:

Test Method: Adhesive tests were measured according to ASTM D-1876. This is a "T" type peel test.

Application of Adhesives to Films: The adhesives were diluted with appropriate solvent so that solids ranged from 12 to 15% and viscosities ranged from S to Y (Gardner Scale). The adhesive solutions were spread onto the films by means of a knife blade and cured at various times and temperatures. Exact curing conditions are given in the tables. The adhesive film thickness ranged between 0.2 to 0.5 mil.

TABLE VII

Adhesive Proportion of Metal and Film Laminates

| Substrate | Adhesive | "B" Stage Condition of Adhesive | Cure Schedule Min. | °C. | psi | Remarks |
|---|---|---|---|---|---|---|
| KAP* to KAP² | Example 14 | 200°C. | 15 | 280 | 264 | Excellent bond. Could not be peeled apart without tearing film. Imprint of glass cloth on film. |
| KAP to KAP¹ | Example 14 | 200°C. | 15 | 280 | 264 | Poor bond. Air pockets and wrinkles in film. |
| AI-8** to AI-8² | Example 14 | 200°C. | 15 | 280 | 250 | Good bond. Smooth bond area. |
| AI-8 to KAP³ | Example 14 | 200°C. | 15 | 280 | 250 | Good bond. Air pockets in film. |
| AI-8 to Cu***¹ | Example 14 | 200°C. | 15 | 280 | 250 | Good bond. Air pockets in film. |
| KAP to Cu³ | Example 14 | 200°C. | 15 | 280 | 250 | Good bond. Could not be peeled apart without tearing film. |
| KAP to KAP³ | Example 14 | 200°C. | 15 | 200 | 250 | Very poor bond. |
| | | | 15 | 250 | 250 | Good bond. |
| | | | 15 | 300 | 250 | Very good bond. |
| KAP to AI-8³ | Example 14 | 200°C. | 15 | 250 | 250 | Good bond. |
| | | | 15 | 300 | 250 | Very good bond. |
| AI-8 to Cu³ | Example 14 | 200°C. | 15 | 280 | 250 | Good bond. |
| KAP to KAP³ | Example 14 | 200°C. | 15 | 280 | 250 | Good bond. Not as strong sample "B" staged to 200°C. |
| | | 200°C. | 15 | 280 | 100 | Fair to good bond. A lot of air pockets in film. |
| KAP to KAP² | Example 14 | 200°C. — Aged 22 days r.t. | 15 | 300 | 250 | Excellent bond. Smooth bond area. |
| KAP to KAP² | Example 14 | 200°C. | 15 | 300 | 200 | Good bond. 5 lbs/inch peel strength. |
| | | | 5 | 300 | 250 | Good bond. 3.5 lbs/inch peel strength. |
| Cu to Cu³ | Example 14 | 200°C. | 15 | 300 | 250 | Good bond. 2 to 3-1/2 lbs/inch peel strength. |
| KAP to KAP³ | Example 14 | 200°C. | 15 | 300 | 250 | Good bond. 2 to 3.5 lbs/inch peel strength. |
| Al*** to Al² | Example 14 | 200°C. | 15 | 300 | 250 | Very good bond. 6 to 9 lbs/inch peel strength. |
| Al to Cu² | Example 14 | 200°C. | 15 | 300 | 250 | Very good bond. 3 to 8 lbs/inch peel strength. |
| Al to Al² | Example 14 | 225°C. | 15 | 300 | 250 | Very good bond. 7 to 8 lbs/inch peel strength. |

*KAP is a polyimide film 1 mil thick derived from 4,4'-diaminophenyl ether and pyromellitic dianhydride and marketed b DuPont under the tradename "Kapton".
**AI-8 is a polyamide-imide film 1 mil thick prepared from pyromellitic dianhydride and 3,4'-diaminobenzanilide in N,N-dime thylacetamide solvent.
***Cu is cold rolled copper 3 mils thick.
****Al is aluminum 3 mils thick.
¹is sandwiched between sheets of metal foil 5 mils thick.
²is sandwiched between sheets of glass cloth and silicone rubber (RTV-60).
³is sandwiched between sheets of asbestos cloth.
⁴is sandwiched between sheets of asbestos cloth and silicone rubber (RTV-60).

TABLE VIII

Peel Strength for Variations in Curing Time, Pressure and Temperature

| Cure Schedule | | | Peel Strength in pounds/inch | |
|---|---|---|---|---|
| Min. | psi | °C. | Cu to Cu | Al to Al |
| 2 | 50 | 300 | 2.0 | — |
| 2 | 100 | 300 | 3.4 | 3.8 |
| 22 | 200 | 300 | 4.0 | 4.5 |
| 2 | 300 | 300 | 5.1 | 5.2 |
| 5 | 50 | 300 | 2.4 | — |
| 5 | 100 | 300 | 3.8 | 4.2 |
| 5 | 200 | 300 | 4.6 | 4.8 |
| 5 | 300 | 300 | 5.6 | 7.0 |
| 15 | 50 | 300 | 2.7 | — |
| 15 | 100 | 300 | 3.9 | 3.9 |
| 15 | 200 | 200 | 4.9 | 6.0 |
| 15 | 300 | 300 | 6.0 | 8.0 |
| 2 | 50 | 250 | 1.65 | — |
| 2 | 100 | 250 | 1.72 | — |
| 2 | 200 | 250 | 1.84 | — |
| 2 | 300 | 250 | 2.76 | — |
| 5 | 50 | 250 | 1.88 | — |
| 5 | 100 | 250 | 2.2 | — |
| 5 | 200 | 250 | 2.5 | — |
| 5 | 300 | 250 | 2.8 | — |
| 15 | 50 | 250 | 3.0 | — |
| 15 | 100 | 250 | 3.5 | — |
| 15 | 200 | 250 | 4.1 | 3.9 |
| 15 | 300 | 250 | 4.6 | — |
| 15 | 250 | 300 | — | 4.0 |

As shown in Table VII the polymer of Example 14 exhibited excellent adhesive properties on all of the substrates listed. Interestingly, the B stage cure of this polymer is sufficiently high in temperature to cause at least partial imidization of the polymer and the polymer still exhibited good bonding properties. As shown, good bonding was still obtained even when the adhesive was B staged by curing at 300°C., although some data in Table VII indicates that the adhesive B staged by fully curing at 300°C. is slightly lower than the adhesive B staged at 200°C. These adhesive properties of the polymer, i.e. its ability to be B staged and/or to be fully cured and maintain its adhesive properties, are not exhibited by conventional polyimides. Another important property of this polymer is that it exhibits good bonding properties with films ranging in thickness from 0.2 mils to 2 mils.

The data shown in Table VII also shows that where the film of "Kapton" polyimide was bonded to itself and to another substrate such as copper the adhesive could not in some cases be peeled without tearing of the film. This indicates that the peel strength was at least as great as the tear strength of the film. In other cases (and under the right conditions), a few inches of the film could be peeled from itself before it tore; in these instances peel strengths from 1 to 5 pounds per inch were obtained.

Table VIII shows the effect of varying the curing time, temperature and pressure on the bond strength. All of the adhesives were D staged at 200°C. prior to bonding. In general, the peel strength increased as the curing time, temperature and pressures were increased, but increase of the pressure and temperature influenced the peel strength more than the increase of curing time. In fact, the time parameter had the same effect on the bond strength at 300°C. as it did at 250°C. At low pressures, 50 psi, variation of the temperature had no great effect on the peel strength. Accordingly, the most important parameter effecting bond strength appeared to be pressure.

The adhesive properties of the polymer of Example 14 with aging were also tested. The polymer was B staged at 200°C. and aged for 22 days at room temperature. There were no deterioration in the adhesive properties that were detectable. Even adhesive samples aged 7 months exhibited fair to good bonds with voids in the adhesive area due to poor bonding procedures.

It should be apparent that the thermoplastic imide polymers of this invention in their B-stage are particularly useful as an adhesive bonding layer on various metallic supporting substrates such as copper, aluminum titanium and stainless steel and other substrates such as resinous sheets or films of high temperature polymers such as aromatic polyimides, aromatic polyamide-imides and aromatic polysulfones. A wet film of a solution of the soluble polymer of this invention may be deposited on the substrate, heated to remove the solvent and partially cure the polymer and provide an adhesive bonding layer on the substrate. The adhesive coated substrate may then be bonded to other materials under heat and pressure. A flexible composite of copper foil and an aromatic polyimide film may, for example, be made by coating either the foil or the film, or both, with the adhesive layer and then bonding the foil and film together. The heretofore described Kapton film is a suitable aromatic polyimide film. Other suitable aromatic polyimide films may be prepared in accordance with the descriptions in U.S. Pat. No. 3,179,614; U.S. Pat. No. 3,179,632, U.S. Pat. No. 3,179,633; and U.S. Pat. No. 3,179,634. Suitable aromatic polyamide-imide films may be prepared from the polymers described in U.S. Pat. No. 3,179,635 and U.S. Pat. No. 3,260,691. The aromatic polyimide films are derived from dianhydrides such as pyromellitic dianhydride or 3,4:3',4'-benzophenonetetracarboxylic dianhydride and an aromatic diprimary diamine such as 4,4'-diaminodiphenyl ether. The aromatic polyamide-imide film may be derived from the aforesaid dianhydrides and aromatic diprimary diamino compounds containing amide linkages such as 3,4'-diaminobenzanilide or they may be derived from the acid chlorides or ester dichlorides of trimellitic anhydride and aromatic diprimary diamino compounds such as 4,4'-diaminodiphenyl ether.

The adhesive coated aromatic polyimide and aromatic polyamide-imide films can be utilized as a flexible cover layer for printed circuits, flat tape cables and similar products produced from supported copper foil. After the circuit or flat cable conductors are etched or otherwise generated on a copper foil laminate, the conductors are exposed and uninsulated. The adhesive coated film can be placed over the exposed conductors and be bonded to the conductors and support so that the conductors are sandwiched between layers of insulation.

While we have described and demonstrated certain present preferred embodiments and uses of our invention, it is to be distinctly understood that the invention is not limited thereto but that it may be otherwise variously embodied and used.

We claim:

1. A dianhydride monomer containing imide linkages and having the structural formula:

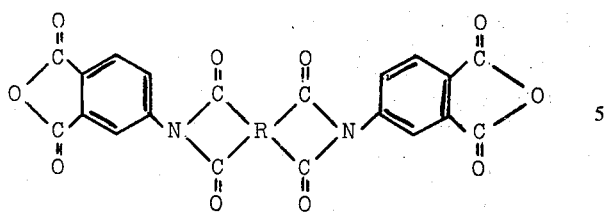

wherein R is selected from the group of tetravelent radicals consisting of:

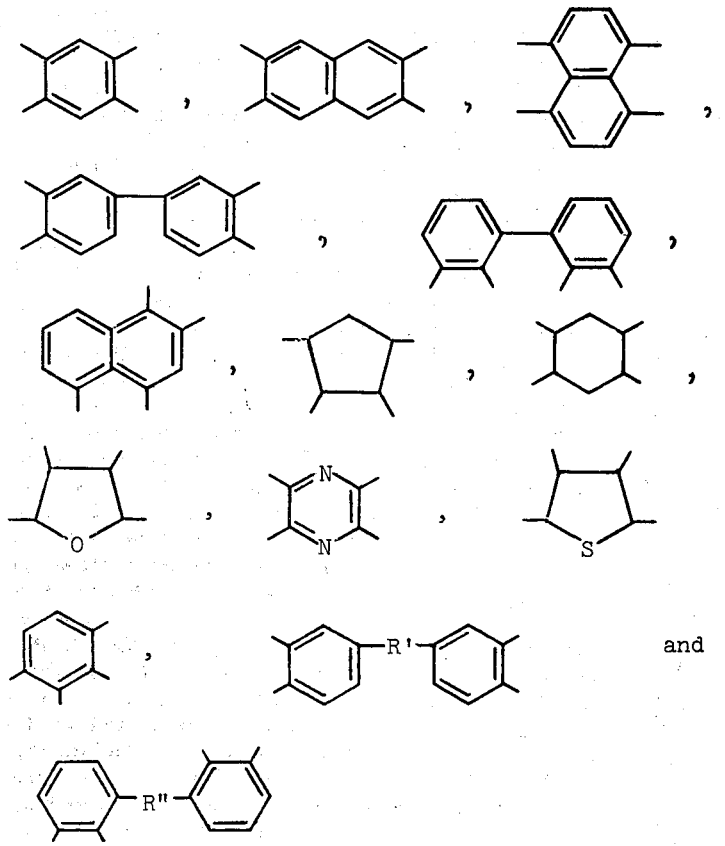

wherein R' is a radical selected from the group consisting of carbonyl, sulfonyl, oxy and alkylene groups of up to 3 carbons and R'' is an alkylene group of up to 3 carbons.

2. The monomer of claim 1 wherein R is selected to provide five membered rings with the adjacent carbonyl and nitrogen groups.

3. The monomer of claim 2 wherein R is selected from radicals having a carbocyclic aromatic ring.

4. The monomer of claim 1 wherein R is

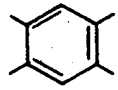

and

5. The monomer of claim 1 wherein R is

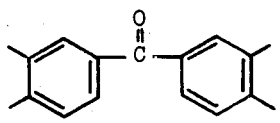

* * * * *